United States Patent [19]

Khan

[11] Patent Number: 5,469,846
[45] Date of Patent: Nov. 28, 1995

[54] IMPLANTABLE NON-ENZYMATIC ELECTROCHEMICAL GLUCOSE SENSOR

[75] Inventor: Shahed U. M. Khan, Pittsburgh, Pa.

[73] Assignee: Duquesne University of the Holy Ghost, Pittsburgh, Pa.

[21] Appl. No.: 312,891

[22] Filed: Sep. 27, 1994

Related U.S. Application Data

[62] Division of Ser. No. 962,667, Oct. 19, 1992, Pat. No. 5,387,327.

[51] Int. Cl.$^6$ ........................................................ A61B 5/05
[52] U.S. Cl. ...................... 128/635; 204/403; 604/891.10
[58] Field of Search ..................................... 128/635, 632; 604/31, 891.1; 204/403, 415

[56] References Cited

U.S. PATENT DOCUMENTS

| | | |
|---|---|---|
| 3,406,109 | 10/1968 | Molloy . |
| 4,059,406 | 11/1977 | Fleet . |
| 4,340,458 | 7/1982 | Lerner et al. . |
| 4,436,094 | 3/1984 | Cerami . |
| 4,496,454 | 1/1985 | Berger . |
| 4,599,157 | 7/1986 | Suzuki et al. . |
| 4,633,878 | 1/1987 | Bombardieri . |
| 4,911,794 | 3/1990 | Parce et al. . |
| 4,919,141 | 4/1990 | Zier et al. . |
| 4,950,378 | 8/1990 | Nagata .................................. 204/403 |
| 5,109,850 | 5/1992 | Blanco .................................. 604/891.1 |

FOREIGN PATENT DOCUMENTS

| | | | |
|---|---|---|---|
| 2287145 | 11/1990 | Japan .................................. 204/403 |
| 1281988 | 1/1987 | U.S.S.R. .................................. 204/403 |

Primary Examiner—Angela D. Sykes
Assistant Examiner—Eric F. Winakur
Attorney, Agent, or Firm—Eckert Seamons Cherin & Mellott; Jolene W. Appleman; Arnold B. Silverman

[57] ABSTRACT

A non-enzymatic implantable blood glucose detector. The detector makes use of a non-reactive tin oxide semiconductor measurement electrode which is suitably energized by an electrical power source. Variations in current density at the measurement electrode are related to variations in glucose content of blood. The device also uses variable voltage to allow the electrode to be self-cleaning.

12 Claims, 4 Drawing Sheets

IMPLANTABLE NON-ENZYMATIC ELECTROCHEMICAL GLUCOSE SENSOR

This is a division of application Ser. No. 07/962,667, filed Oct. 19, 1992, now U.S. Pat. No. 5,387,327.

BACKGROUND OF THE INVENTION

1. Field of the Invention

This invention relates to an implantable sensor for making amperometric measurements in body fluids, such as blood or tissue liquid, with a measurement electrode. More specifically, the invention relates to a sensor that detects blood glucose levels in vivo and initiates the automatic dispensing of insulin if detected blood glucose levels exceed a desired set point.

2. Description of the Prior Art

A patient suffering from the metabolic disease diabetes mellitus must balance his or her blood sugar level several times daily by injection of insulin. In addition, blood sugar controls are required in order to protect the patient against substantial metabolic deviations. These blood sugar controls typically require pricking the patient's finger tip to draw blood, an inconvenience for all patients and a substantial burden for small children and adolescents.

In order to assist in the control of blood sugar, electrochemical enzyme sensors have been used to determine blood glucose in vitro. Many of these devices, however, are quite expensive and heavy in their construction, such that they can be considered only for stationary treatment programs.

The use of implantable enzyme sensors has also been proposed. See, e.g. Zier, et al., U.S. Pat. No. 4,919,141. A significant disadvantage of these and other enzymatic sensors is that they cannot be used continuously, as they rely on platinum electrodes which react too quickly with body fluids to offer continuous, long-term service. Consequently, implantable enzyme sensors have a useful life of relatively short duration.

Still another disadvantage of prior art sensors is the tendency for the measurement electrode to become coated with deposits of biological materials, which impede performance. This problem is especially acute in implantable units, which become less effective over time as a result of the encrustation of the electrode.

Parce et al., U.S. Pat. No. 4,911,794, discloses the use of semiconductive electrodes for analyte measurement using a zero volume cell. The patent discloses the use of a number of semiconductive electrodes, such as silicon and gallium arsenide, as well as gallium selenide or aluminum gallium arsenide as the working or sensor electrode. Parce et al. is not, however, concerned with an implantable unit for measuring blood glucose.

Lerner et al., U.S. Pat. No. 4,340,458, discloses an electrochemical glucose sensor having a glucose oxidation electrode and a glucose-permeable membrane that separates the electrode from high molecular weight compounds. The electrodes of this reference are teflon-bonded platinum and silver/silver-chloride. Neither would be acceptable for an implantable glucose sensor. Obtaining a glucose concentration dependent signal by use of a platinum electrode is unreliable, non-reproducible and non-specific, as platinum reacts with almost anything. Furthermore, platinum does not oxidize or reduce glucose, rather oxidizes and reduces phosphate in the presence of glucose.

Cerami, U.S. Pat. No. 4,436,094, discloses a method for continuous, in vivo measurement of glucose in body fluids, such as blood, using a glucose monitor including an electrode with a charge-transfer medium comprising a reversible complex of a binding micromolecular component and a charge-bearing carbohydrate component. The electrode is enclosed in a semi-permeable membrane, selectively permeable to glucose.

Bombardineri, U.S. Pat. No. 4,633,878, discloses an implantable device for automatic insulin or glucose infusion in diabetic subjects, based on the continuous monitoring of the patient's glucose levels. The device uses an enzymatic-pontentiometric glucose sensor. The reference also discloses the use of hollow fibers, which form a filter through which only low molecular weight molecules may pass.

In spite of the above teachings, there is a need for an implantable electrochemical sensor capable of infusing medicines, such as insulin, when needed.

SUMMARY OF THE INVENTION

The present invention has solved the above noted problems by providing a non-enzymatic blood glucose detector having a non-reactive semiconductor measurement electrode, preferably tin oxide or titanium dioxide, energized by an electrical power source, such as a battery, and disposed within a tubular sleeve comprising a reference electrode and a counter electrode. The sleeve has an opening therein for permitting glucose molecules to pass through the sleeve to the measurement electrode, but resist, and preferably preclude the passage of molecules sized greater than glucose, preferably greater than about 100,000 M.W., such as lipids, protein, and other large molecules. Amino acids and urea do not effect the signal of the measurement electrode. The measurement electrode is connected to a monitoring device for monitoring current density at the measurement electrode, in response to glucose oxidation or glucose reduction reactions taking place at the electrode. The current density at the measurement electrode is translated into a blood glucose level by the monitoring device, which may be a microprocessor.

The detector may be an implantable unit adapted for delivering insulin in response to detection by the monitoring device of blood glucose levels exceeding a predetermined set point. In this case, the unit includes an insulin reservoir and insulin pump for delivering insulin from the reservoir to the patient in response to a signal from the microprocessor.

It is an object of the invention to provide an implantable electrochemical sensor that may be used continuously by the patient.

It is another object of the invention to provide a non-enzymatic electrochemical sensor.

It is still another object of the invention to provide an implantable electrochemical sensor that may be used over relatively long periods of time without need of replacement.

It is yet another object of the invention to provide an electrochemical sensor having a self-cleaning measurement electrode.

It is another object of the invention to provide an implantable electrochemical sensor that uses a non-reactive but glucose specific measurement electrode.

These and other advantages of the invention will become readily apparent as the following detailed description of the preferred embodiments proceeds, with reference to the illustrations appended hereto.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

As used herein, the term "non-reactive semiconductor electrode" means an electrode formed of a semiconductive material that does not appreciably react electrochemically with body fluids, such as blood, over extended time periods, such as tin oxide or titanium dioxide.

As used herein, the term "patient" shall be deemed to include humans and animals.

Figure 1:
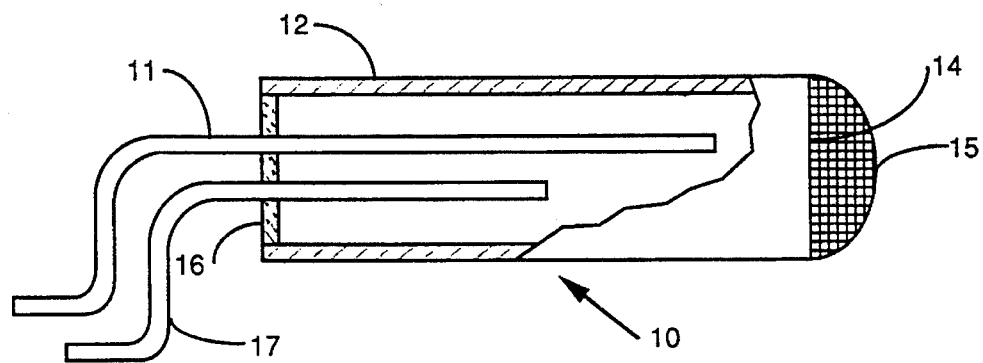
FIG. 1 is a cross sectional schematic illustration of a preferred detector of the invention.

Referring to FIG. 1, there is shown generally a non-enzymatic electrochemical sensor 10 having a non-reactive semiconductor measurement electrode 11, preferably made of tin oxide or titanium dioxide, which is disposed within a counter electrode, or sleeve, 12. A reference electrode, 17 is also positioned within the sleeve 12. The sleeve 12, as well as any other implantable component of the invention having direct contact with the body and its fluids, other than the measurement electrode 11, may be fabricated of any biocompatible material such as stainless steel, titanium, ceramic, etc. The non-reactive measurement electrode 11 is energized by an electrical power source, such as a lithium iodide battery, 2.7 V, in order to supply a voltage of 1 volt with respect to the reference electrode 17 to provide a current density at the measurement electrode 11 of about 200 to about 500 micro amps/cm$^2$.

The sleeve 12 is opened at one end 14, which is covered by a biocompatible membrane 15. This membrane allows glucose molecules to enter the opening 14 in the sleeve 12, where the glucose may be sensed by the non-reactive measurement electrode 11. The membrane 15 is sized to keep larger molecules, such as those having greater than 100,000 molecular weight, for example proteins and lipids, from passing through. These larger molecules would interfere with the measurement being made by the non-reactive electrode 11 A pore cellulose membrane has been used as the biocompatible membrane for purposes of the invention. Among the preferred materials suitable for use as the membrane 15 are cellulose esters, nylon polyvinyl fluoride, polytetrafluoroethylene, cellulose nitrate, acetate, and mixtures thereof. The membrane is made of cellulose, supplied, for example, by Micon Co. The preferred membrane has a maximum pore size that allows molecules having less than 100,000 dalton (YM 100) through. The other end of the detector 10 is sealed with an insulating ring 16 as illustrated.

Figure 2:
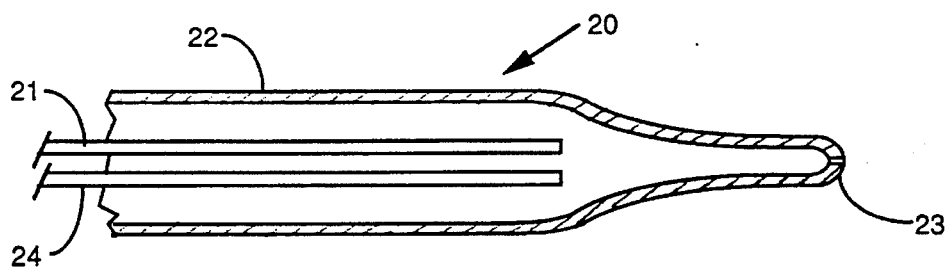
FIG. 2 is a cross sectional schematic illustration of another preferred detector of the invention.

FIG. 2 illustrates an alternative embodiment for an electrochemical sensor 20 having a venturi-type sleeve 22 (counter electrode) surrounding a micro electrode 21. In this embodiment, the micro electrode 21 is also preferably a semiconductor fabricated of tin oxide or titanium dioxide. The detector 20 of FIG. 2 has a restricted end 23 having a very small opening therein which allows the passage therethrough of glucose molecules, but which does not allow the passage of molecules larger than 100,000 M.W. A reference electrode 24 is also positioned within the sleeve 22 as shown. In this embodiment the cellulose membrane is not required.

In both the embodiments of FIG. 1 and 2 a pump is employed to pump the fluid in and out of the sleeve 12 22.

The use of a tin oxide or titanium dioxide measurement electrode as contemplated by the invention allows greater stability for the electrode than would be possible with, for example, platinum electrodes, which tend to be too reactive. In contrast, the tin oxide or titanium dioxide semiconductor measurement electrode of the invention is relatively non-reactive and therefore can be used continuously and over extended time periods.

The electrode surface is preferably about 1 cm$^2$, for example, in the form of tin oxide or titanium oxide coated thin wires of 0.2 cm diameter and a length 1.6 cm or 0.4 cm diameter and 0.8 cm long. A thin tin oxide or titanium oxide layer can be put on a platinum or nickel wire by spray pyrolyric deposition using ethanolic 0.1 m tin chloride or 0.1 m titanium chloride solution at a substrate temperature of 400°–500° C. The carrier gas for the spray solution should be oxygen. Tin oxide coated glass can also be used as the sensor electrode.

Figure 3:
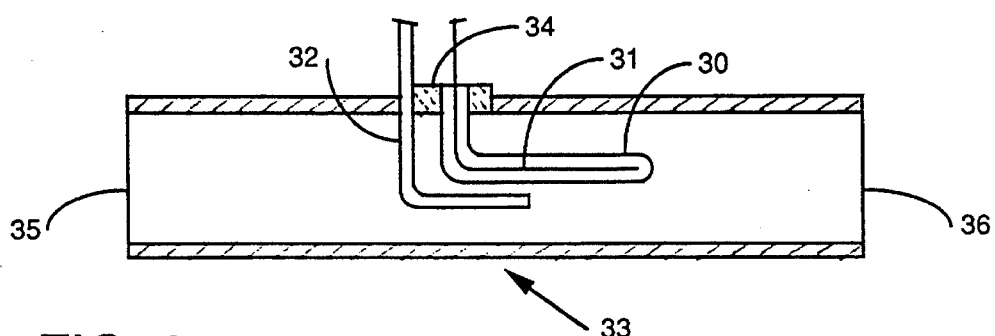
FIG. 3 is a cross sectional schematic illustration of another preferred detector of the invention.

FIG. 3 illustrates another alternative embodiment for a non-enzymatic electrochemical sensor of the invention. In this embodiment body fluid is not needed to be pumped in and out of the sleeve 33. Rather, both sides of the sleeve 33 are open and the sensor electrode 30 is locally covered with a cellulose membrane (YM 100) 30 which allows only molecules < 100,000 MW to pass through. In FIG. 3, the sensor 31 is preferably tin oxide or titanium coated platinum or nickel wire. The reference electrode 32 is also positioned inside the sleeve or counter electrode 33. The counter electrode 33 may be fabricated of, for example, titanium. An insulating grid 34 is positioned around the sensor electrode 31 as illustrated. The sleeve 31 of the FIG. 3 embodiment has two open ends 35 and 36, as illustrated.

Figure 4:
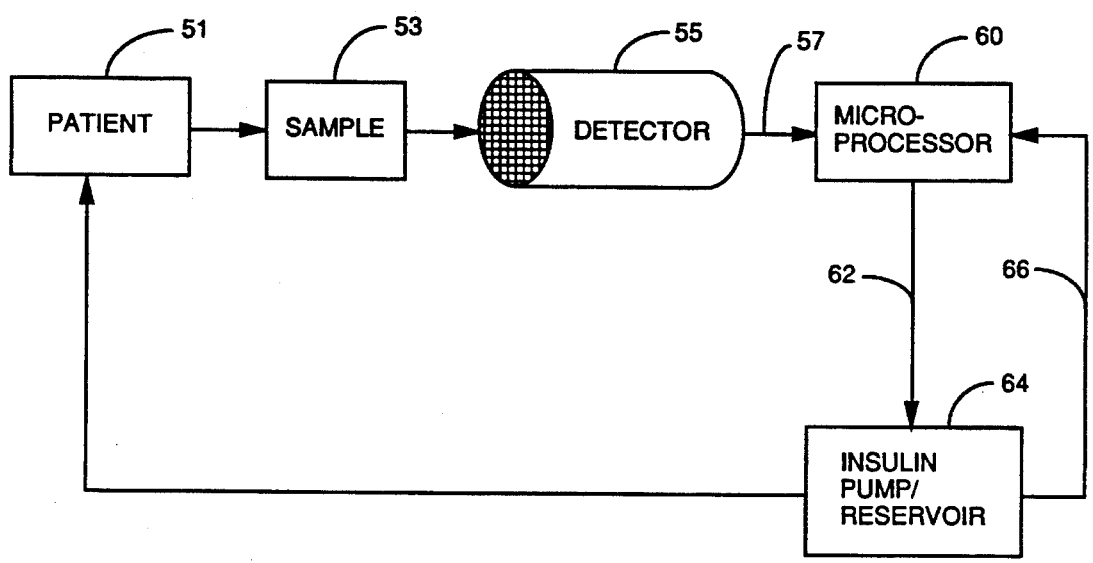
FIG. 4 is a block circuit diagram of a preferred implantable glucose sensor and insulin delivery system of the invention.

FIG. 4 illustrates a block circuit diagram for an implantable insulin delivery system of the invention. A patient 51 passes a sample 53, such as blood, through the detector 55, which screens the larger molecules and allows the glucose in the blood to pass through and into contact with the non-reactive electrode contained therein. This electrode, not shown, is energized by a power source, such as a battery, also not shown. The glucose within the sample in the vicinity of the measurement electrode undergoes an oxidation reaction under applied positive voltages.

The current density at the non-reactive measurement electrode is proportional to the amount of glucose present in the sample 53, and this current density can be used as a signal 57 which may be fed to a microprocessor 60 for comparison to predetermined set points of blood glucose levels.

The predetermined set point of blood glucose should be about 140 mg/dl of blood. This concentration of glucose will give a signal of about 500 micro amps/cm$^2$. When this amount of current density is fed into the microprocessor the microprocessor signals the drug delivery system to inject a fixed amount of drug insulin.

If the microprocessor 60 detects that the signal 57 corresponds to blood glucose levels exceeding these set points, the microprocessor 60 may send a signal 62 to an insulin pump/reservoir 64, which can automatically pump insulin to the patient 51 from a self-contained reservoir. This pumping proceeds until the microprocessor, through loop 66, receives a signal that glucose levels have stabilized, at which point the pump is shut down.

The implantable unit can also include a glucose pump and reservoir, adapted to infuse glucose to the patient upon detection of blood sugar levels below a desired set point.

In a highly preferred embodiment to the invention, the measurement electrode 11, 21, and 31 is powered with a power source that creates a variable voltage. Preferably, voltages of −0.4 to +1.0 V are used.

The variable voltage can be supplied by a tiny voltage scanner which continuously scans voltage from −0.4 Volt to 1.0 Volt with respect to the reference electrode (Ag/AgCl) and back again with a scan rate of 200 mY/sec.

The variable voltage allows the measurement electrode to be self-cleaning, and thereby avoids problems with prior electrodes, that tend to become encrusted with deposits.

Figure 5:
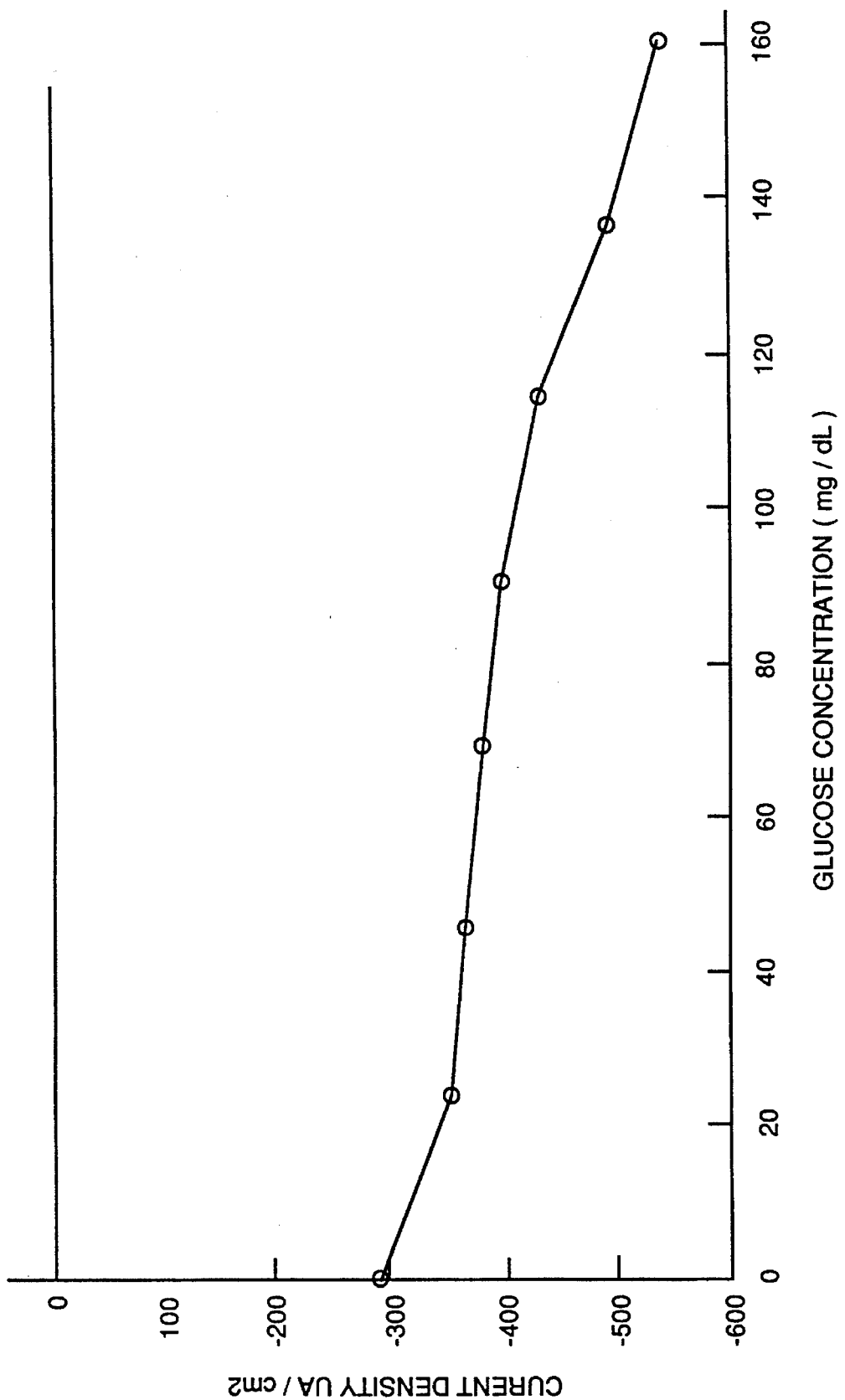
FIG. 5 is a graph illustrating the current density versus glucose concentration in blood plasma filtered through a YM100 membrane.

FIG. 5 illustrates that the current density at the measurement electrode of the invention increases with the increase of glucose concentration in blood. As the concentration of glucose goes above the normal concentration level by 0 to 160 mg/dL, the current density increases from −300 microamps per cm$^2$ to −550 microamps per cm$^2$. This is an easily detectable change in current density.

The detector functions by allowing the change in current density associated with a change in glucose levels to be measured as a result of glucose oxidation or reduction reactions occurring at the measurement electrode, which changes in current density are translated into changes in blood glucose level by the microprocessor 60 (FIG. 4). Typically, a preferred set point for activating the insulin pump 64 would occur if blood glucose levels of the patient exceed about 150 mg per/dL. This set point would, of course, vary from patient to patient.

Figure 6:
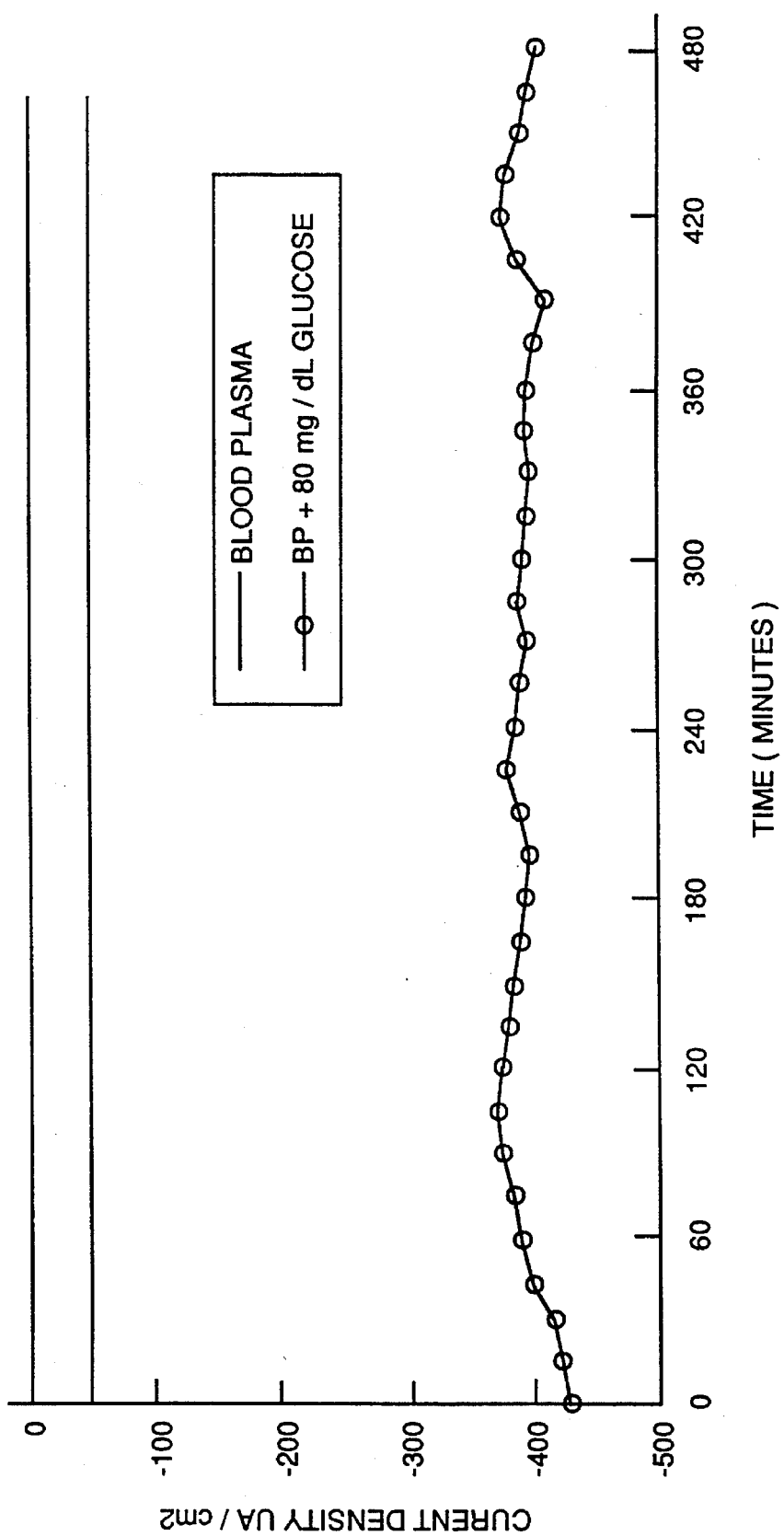
FIG. 6 is a graphical illustration of current density versus time in blood plasma and 80 mg/dL glucose filtered through a YM100 membrane.

FIG. 6 shows that no decrease in signal is observed for as long as 480 minutes (8 hours) when a tin oxide electrode of the invention is placed in blood plasma, provided that the electrode is covered with a 100,000 molecular weight cellulose membrane. This demonstrates the potential for consistent, long-term use of the invention.

The implantable unit may be implanted in the patient in any number of ways that comprise no part of the invention. For example, it would be possible to implant the measurement electrode/sleeve assembly in the patient's podal vein where glucose concentration variation could be easily monitored, and implant the remainder of the apparatus, such as battery, insulin pump and microprocessor, within the thoracic cavity of the patient.

While specific embodiments of the invention have been described in detail, it will be appreciated by those skilled in the art that various modifications and alternatives to those details could be developed in light of the overall teaching of the disclosure. Accordingly, the particular arrangements disclosed are meant to be illustrative only and not limiting as to the scope of the invention, which is to be given the full breadth of the appended claims and any and all equivalents thereof. Additionally, although a number of objects of the invention have been recited herein, it is specifically intended that the claims, and not the objects, define the scope of the invention.

I claim:

1. A method of detecting changes in blood glucose levels, comprising:

providing an implantable non-enzymatic blood glucose detector having a non-reactive semiconductor measurement electrode energized by a battery means and disposed within a sleeve member having an opening permitting glucose molecules to pass therethrough to said measurement electrode, but resisting the passage therethrough of molecules of predetermined greater size;

connecting said measurement electrode to a monitoring means for monitoring a current density at said measurement electrode in response to glucose molecule oxidation or glucose molecule reduction reactions at said measurement electrode:

continuously passing blood through said sleeve opening to said measurement electrode;

continuously monitoring said current density by said monitoring means; and translating changes in current density detected by said monitoring means to changes in blood glucose levels.

2. The method of claim 1 employing as material for said semiconductor measurement electrode a semiconductor selected from the group consisting of tin oxide and titanium dioxide.

3. The method of claim 2 employing said sleeve member opening covered with a biocompatible membrane sized to permit glucose molecules to pass therethrough, but to preclude passage therethrough of molecules sized greater than about 100,000 M.W.

4. The method of claim 1 employing as said sleeve member a venturi sleeve having a restricted opening for allowing said glucose molecules to pass therethrough, but precluding passage therethrough of molecules larger than about 100,000 M.W.

5. The method of claim 1 employing said battery means at a variable voltage, thereby maintaining said measurement electrode in a clean state.

6. A method of delivering insulin within a patient comprising:

providing an implantable non-enzymatic blood glucose unit comprising an implantable non-reactive semiconductor measurement electrode, said electrode energized by an electrical power source and disposed within a sleeve member having an opening permitting glucose molecules to pass therethrough to said measurement electrode, but precluding the passage therethrough of molecules sized greater than about 100,000 M.W., said unit further comprising monitoring means connected to said electrode for monitoring current density at said measurement electrode, said unit further including an insulin reservoir and insulin pump;

implanting said unit in a patient;

continuously passing blood from said patient through said sleeve opening to said measurement electrode;

continuously monitoring changes in current density at said measurement electrode in response to glucose molecule oxidation or glucose molecule reduction reactions at said measurement electrode, with said monitoring means;

translating changes in current density detected by said monitoring means to changes in blood glucose levels; and delivering insulin from said insulin reservoir to said patient via said insulin pump in response to changes in current density detected by said monitoring means in response to changes in blood glucose levels from a normal glucose level to a glucose level exceeding a predetermined set point.

7. The method of claim 6 employing as said electrical power source a battery means.

8. The method of claim 6 employing as a material for said semiconductor electrode a semiconductor selected from the group consisting of tin oxide and titanium dioxide.

9. The method of claim 8 employing said sleeve member opening covered with a biocompatible membrane sized to permit glucose molecules to pass therethrough, but to preclude passage therethrough of molecules sized greater than about 100,000 M.W.

10. The method of claim 8 employing as said sleeve member a venturi sleeve having a restricted opening for allowing said glucose molecules to pass therethrough, but precluding passage therethrough of molecules sized greater than about 100,000 M.W.

11. The method of claim 6 employing said electrical power source at a variable voltage, thereby maintaining said measurement electrode in a clean state.

12. The method of claim 6 further employing with said unit a glucose reservoir and glucose pump, said method including the step of delivering glucose to said patient via said glucose pump in response to current density changes detected by said monitoring means corresponding to changes in blood glucose levels from a normal glucose level to a glucose level below a predetermined set point.

\* \* \* \* \*

UNITED STATES PATENT AND TRADEMARK OFFICE
CERTIFICATE OF CORRECTION

PATENT NO. :   5,469,846
DATED      :   November 28, 1995
INVENTOR(S) :  SHAHED U. M. KHAN It is certified that error appears in the above-indentified patent and that said Letters Patent is hereby corrected as shown below:

Column 3, line 55, a period --.-- should be inserted after "electrode 11".

Column 5, line 19, "mY/sec" should be --mV/sec--.

Claim 8, column 7, line 6, --measurement-- should be inserted before "electrode".

Signed and Sealed this

Seventh Day of January, 1997

*Attest:*

BRUCE LEHMAN

*Attesting Officer*        Commissioner of Patents and Trademarks